US010012650B2

(12) United States Patent
Bender et al.

(10) Patent No.: US 10,012,650 B2
(45) Date of Patent: Jul. 3, 2018

(54) ASSAYS FOR BTK INHIBITORS

(71) Applicant: Merck Patent GmbH, Darmstadt (DE)

(72) Inventors: Andrew Bender, Reading, MA (US); Lesley Liu-Bujalski, Bedford, MA (US); Albertina Pereira, Bedford, MA (US); Richard D. Caldwell, Brookline, MA (US); Roland Grenningloh, Arlington, MA (US); Daigen Xu, Westford, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/964,945

(22) Filed: Dec. 10, 2015

(65) Prior Publication Data

US 2016/0169894 A1 Jun. 16, 2016

Related U.S. Application Data

(60) Provisional application No. 62/090,648, filed on Dec. 11, 2014.

(51) Int. Cl.
| | |
|---|---|
| *G01N 33/573* | (2006.01) |
| *C07D 495/04* | (2006.01) |
| *G01N 33/53* | (2006.01) |
| *G01N 33/574* | (2006.01) |
| *G01N 33/58* | (2006.01) |
| *C07F 5/02* | (2006.01) |

(52) U.S. Cl.
CPC ......... *G01N 33/573* (2013.01); *C07D 495/04* (2013.01); *C07F 5/022* (2013.01); *G01N 33/53* (2013.01); *G01N 33/57484* (2013.01); *G01N 33/58* (2013.01); *G01N 2333/912* (2013.01); *G01N 2500/02* (2013.01)

(58) Field of Classification Search
CPC ..... C07D 495/04; C07F 5/022; G01N 33/573; G01N 33/53; G01N 33/57484; G01N 33/58; G01N 2333/912; G01N 2500/02
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese |
| 5,602,273 A | 2/1997 | Giese |
| 5,604,104 A | 2/1997 | Giese |
| 5,610,020 A | 3/1997 | Giese |
| 5,650,270 A | 7/1997 | Giese |
| 8,987,233 B2 * | 3/2015 | Pan ............... C07D 487/04 514/262.1 |
| 2016/0264548 A1 * | 9/2016 | Qiu ............... C07D 403/12 |

FOREIGN PATENT DOCUMENTS

| | | | |
|---|---|---|---|
| WO | 2008054827 A2 | 5/2008 | |
| WO | WO-2009158571 A1 * | 12/2009 | ........... C07D 239/47 |
| WO | 2011090760 A1 | 7/2011 | |
| WO | 2014059368 A1 | 4/2014 | |
| WO | 2015048662 A2 | 4/2015 | |
| WO | 2015061247 A2 | 4/2015 | |
| WO | 2016010961 A1 | 1/2016 | |

OTHER PUBLICATIONS

Baskin et al., Proc. Natl. Acad. Sci. Usa, 2007, 104:16793-16797.
Berge et al., J. Pharmaceutical Sciences, 1977, 66(1):1-19.
Ellmeier et al., J. Exp. Med. 2000, 192(11):1611-1623.
Feldhahn et al., J. Exp. Med., 2005, 201(11):1837-1852.
Foster, Adv. Drug Res., 1985, 14:1-40.
Gillette et al., Biochemistry, 1994, 33(10):2927-2937.
Hanzlik et al., J. Org. Chem., 1990, 55(13):3992-3997.
Horwood et al., J Exp Med, 2003, 197(12)1603-1611.
Hunter T., Cell, 1987, 50(5):823-829.
Islam and Smith, Immunol. Rev., 2000, 178:49-63.
Iwaki et al., J. Biol. Chem., 2005, 280(48):40261-40270.
Jansson and Holmdahl, Clin. Exp. Immunol.,1993, 94:459-465.
Jarman et al., Carcinogenesis, 1995, 16(4):683-688.
Khan et al., Immunity, 1995, 3:283-299.
Lindvall et al., Immunol. Rev., 2005, 203:200-215.
Pan et al., Chem. Med Chem., 2007, 2:58-61.
Rastetter et al., Annu Rev Med, 2004, 55:477-503.
Reider et al., J. Org. Chem., 1987, 52:3326-3334.
Rosen et al., New Eng. J. Med., 1995, 333(7):431-440.
Rostovtsev et al., Angew. Chem. Int. Ed. 2002, 41:2596-99.
Smith M.B. and March J., "March's Advanced Organic Chemistry", 5th Ed., Ed., John Wiley & Sons, New York, 2001.
Sorrell Thomas Organic Chemistry University Science Books, Sausalito, 1999.
Sun et al., Bioconjugate Chem., 2006, 17(1):52-57.
Periodic Table of the Elements, CAS version, Handbook of Chemistry and Physics, 75th Ed.
Evans et. al., J. Pharm. Exp. Ther., 2013, 346(2): 219-228.
Honigberg et. al., Proc. Nat. Acad. Sci., 2010, 107(29): 13075-13080.
Simon et al., Nature Chem. Biol., 2013, 9(4): 200-205.

* cited by examiner

*Primary Examiner* — Shafiqul Haq
(74) *Attorney, Agent, or Firm* — Dwight D. Kim; EMD Serono Research and Development Institute

(57) ABSTRACT

The present invention relates to BTK occupancy assays.

4 Claims, 1 Drawing Sheet

MSD assay results.
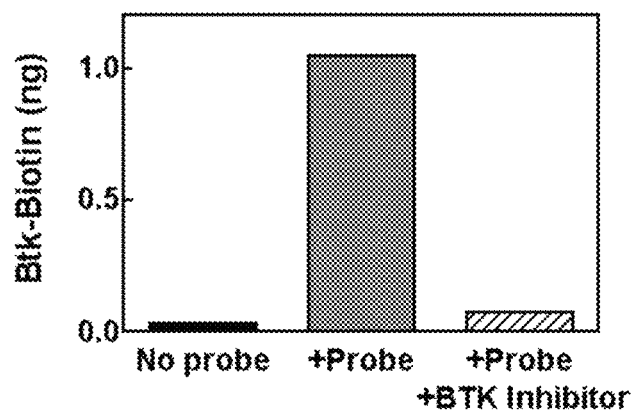

ASSAYS FOR BTK INHIBITORS

RELATED APPLICATION

This application claims the benefit of U.S. Provisional Application Ser. No. 62/090,648, filed on Dec. 11, 2014. The content of the aforementioned application is hereby incorporated by reference in its entirety.

TECHNICAL FIELD OF THE INVENTION

The present invention relates to assays that are used in combination with Bruton's Tyrosine Kinase (BTK) inhibitors.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling, they provide a target to modulate cellular function with small molecular kinase inhibitors and thus make good drug targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology, such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from the BCR. Lack of BTK has been shown to reduce BCR signaling and therefore inhibition of BTK could be a useful therapeutic approach to block B-cell mediated disease processes. Also, BTK has been reported to play a role in apoptosis (Islam and Smith Immunol. Rev. 2000 178:49,) and thus BTK inhibitors are useful for the treatment of certain B-cell lymphomas and leukemias (Feldhahn et al. J. Exp. Med. 2005 201:1837).

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models and treatment with BTK inhibitors. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has demonstrated dose-dependent efficacy in a mouse arthritis model (Z. Pan et al., Chem. Med Chem. 2007 2:58-61).

BTK is also expressed by cells other than B-cells that may be involved in disease processes. BTK is key component of Fc receptor signaling in myeloid cells. For example, BTK is expressed by eosinophils and mast cells and BTK-deficient bone marrow derived mast cells demonstrate impaired antigen induced degranulation (Iwaki et al. J. Biol. Chem. 2005 280:40261). This shows BTK could be useful for treating pathological mast cell responses such as in allergy and asthma. Also, monocytes from XLA patients, in which BTK activity is absent, show decreased TNF-alpha production following stimulation (Horwood et al. J Exp Med 197:1603, 2003). Therefore TNF-alpha mediated inflammation could be modulated by small molecular BTK inhibitors.

An important aspect of understanding how any potential therapeutic is acting is knowing the level of engagement of the drug target by the molecule after its administration to human subjects. The measurement of this pharmacodynamic (PD) activity provides guidance for appropriate dosage selection to optimize inhibition of the drug target and also correlation of target inhibition with disease treatment efficacy. This type of information is crucial for successful evaluation of candidate drugs in trials and subsequent usage in clinical practice. Inhibitors of BTK typically bind to the active site of the enzyme and "occupy" that space, thus preventing catalysis and enzyme activity. The proposed invention measures how much of the BTK in a sample is occupied or unoccupied after administration of a BTK inhibitor. By determining occupancy, the invention provides a measure of the percent of BTK inhibited and thus a PD readout of the level of inhibition achieved by administration of the inhibitor compound.

SUMMARY OF THE INVENTION

It has now been found that compounds of this invention are effective as probe compounds to measure the occupancy of BTK. Such compounds have general formula I:

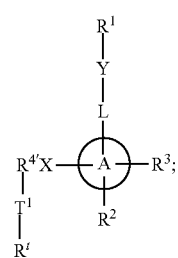

wherein each of $R^1$, $R^2$, $R^3$, $R^{4'}$, X, Y, L, $T^1$ and $R^t$ is as defined and described in embodiments herein.

FIGURES

FIG. 1. BTK occupancy assay MSD results.

DETAILED DESCRIPTION

1. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_1$-4 straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure

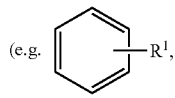

refers to at least

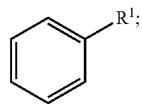

and

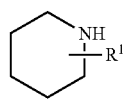

refers to at least

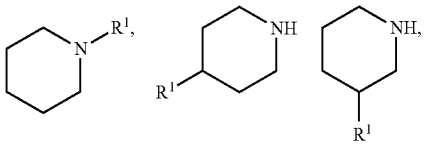

or

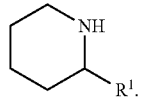

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_1$-4 aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O— heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH— aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$-heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH—-alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)— heteroaryl, —S(O)-heterocyclyl —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$—alkynyl, —NHSO$_2$— carbocyclyl, —NHSO$_2$— aryl, —NHSO$_2$-heteroaryl, —NHSO$_2$-heterocyclyl,
—CH$_2$NH$_2$, —CH$_2$SO$_2$CH$_3$,
-mono-, di-, or tri-alkyl silyl,
-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S— aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less than about 50 µM, less than about 1 µM, less than about 500 nM, less than about 100 nM, or less than about 10 nM.

The terms "measurable affinity" and "measurably inhibit," as used herein, means a measurable change in BTK activity between a sample comprising a compound of the present invention, or composition thereof, and BTK, and an equivalent sample comprising BTK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

2. Description of Exemplary Compounds

In one aspect, the invention provides an assay for determining drug target occupancy, comprising a probe.

In one aspect, the invention provides an assay for determining drug target occupancy in a patient receiving a BTK kinase inhibitor therapy, comprising a probe.

According to one aspect, the present invention provides a kit for determining drug target occupancy in a patient receiving a BTK kinase inhibitor therapy, comprising a probe.

In another aspect, the invention provides a method for determining drug target occupancy of a BTK inhibitor compound, comprising:

(a) contacting a sample comprising a mixture of BTK kinase and a BTK inhibitor compound, with a probe to form a probe-bound kinase;

(b) detecting the amount of probe-bound kinase in the sample; and (c) determining the occupancy of the BTK inhibitor compound based on the amount of probe-bound kinase detected in the sample.

In another aspect, the invention provides a method for determining drug target occupancy in a subject receiving a BTK kinase inhibitor therapy, comprising:

(a) dosing the subject with a BTK inhibitor compound;

(b) collecting a biological sample (e.g., blood or spleen) from the subject;

(c) contacting the sample with a probe to form a probe-bound BTK kinase;

(d) detecting the amount of probe-bound BTK kinase in the sample; and (e) determining target occupancy of the BTK kinase based on the amount of probe-bound kinase detected in the sample.

In another aspect, the invention provides a method for determining drug target occupancy in a patient receiving a BTK kinase inhibitor therapy, comprising:

(a) contacting a sample comprising a BTK kinase with a probe to form a probe-bound kinase, wherein the sample is obtained from the patient following administration of at least one dose of an irreversible BTK kinase inhibitor;

(b) detecting the amount of probe-bound kinase in the sample; and (c) determining target occupancy of the BTK kinase based on the amount of probe-bound kinase detected in the sample.

In another aspect, the invention provides a method for monitoring drug target occupancy in a patient receiving a BTK kinase inhibitor therapy.

In certain embodiments, the probe is a compound of formula I,

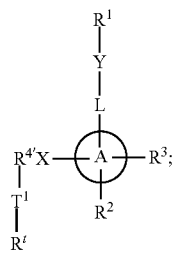

wherein:
Ring A is a 6-membered heteroaryl ring having 1 or 2 nitrogens, selected from pyridine, pyrazine, pyridazine, and pyrimidine;
$R^2$ is selected from —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
$R^3$ is selected from —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
wherein at least one of $R^2$ or $R^3$ is —C(O)N(R)$_2$, or CN;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
L is a divalent group selected from $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, and a 5-6 membered monocyclic heteroaryl ring having 1-4 heteroatoms independently selected from nitrogen, oxygen, or sulfur; each of which is optionally substituted; or L is a divalent group selected from $C_{1-6}$ aliphatic-$C_{3-10}$ aryl, $C_{1-6}$ aliphatic-3-8 membered saturated or partially unsaturated carbocyclic ring, $C_{1-6}$ aliphatic-3-7 membered heterocyclic ring having 1-4 heteroatoms independently selected from nitrogen, oxygen, or sulfur, and a $C_{1-6}$ aliphatic-5-6 membered monocyclic heteroaryl ring having 1-4 heteroatoms independently selected from nitrogen, oxygen, or sulfur; each of which is optionally substituted;
Y is O, S, SO$_2$, SO, C(O), CO$_2$, C(O)N(R), —NRC(O), —NRC(O)N(R), —NRSO$_2$, or N(R); or Y is absent;
$R^1$ is a Michael acceptor selected from $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, and a 5-6 membered monocyclic heteroaryl ring having 1-4 heteroatoms independently selected from nitrogen, oxygen, or sulfur; each of which is optionally substituted;
X is O, S, SO$_2$, SO, C(O), CO$_2$, C(O)N(R), —NRC(O), —NRC(O)N(R), —NRSO$_2$, or N(R); or X is absent; and
$R^{4'}$ is a divalent group selected from $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, and a 5-6 membered monocyclic heteroaryl ring having 1-4 heteroatoms independently selected from nitrogen, oxygen, or sulfur; each of which is optionally substituted;
$T^1$ is a bivalent tethering moiety; and
$R^t$ is a detectable moiety.

In certain embodiments, the probe is a compound of formula I-a, I-b, I-c, or I-d:

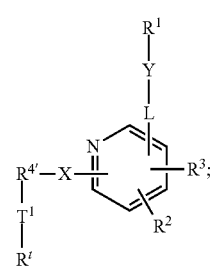

I-a

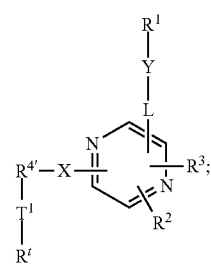

I-b

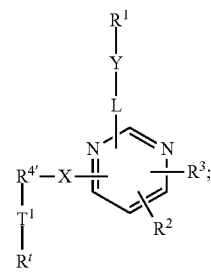

I-c

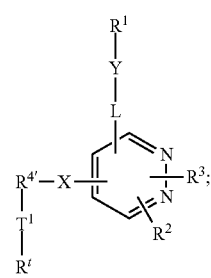

I-d wherein each of $R^1$, $R^2$, $R^3$, $R^4$, X, L and Y is as defined above and described in embodiments, classes and subclasses above and herein, singly or in combination.

In certain embodiments of any of the formulae herein, $R^2$ is hydrogen, halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, $R^2$ is halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, $R^2$ is halogen, —C(O)R, —CO$_2$R, —C(O)N(R)$_2$, —NRC(O)R, —NRC(O)N(R)$_2$, or —NRSO$_2$R. In certain embodiments, $R^2$ is halogen or —C(O)N(R)$_2$.

In certain embodiments of any of the formulae herein, $R^2$ is F or —C(O)NH$_2$. In certain embodiments, $R^2$ is F. In certain embodiments, $R^2$ is —C(O)NH$_2$. In certain embodiments, $R^2$ is —CN.

In certain embodiments of any of the formulae herein, $R^2$ is hydrogen.

In certain embodiments of any of the formulae herein, $R^3$ is hydrogen, halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, $R^3$ is halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, $R^3$ is halogen, —C(O)R, —CO$_2$R, —C(O)N(R)$_2$, —NRC(O)R, —NRC(O)N(R)$_2$, or —NRSO$_2$R. In certain embodiments, $R^3$ is halogen or —C(O)N(R)$_2$.

In certain embodiments of any of the formulae herein, $R^3$ is NH$_2$, Cl, F or —C(O)NH$_2$. In certain embodiments, $R^3$ is F. In certain embodiments, $R^3$ is —C(O)NH$_2$. In certain embodiments, $R^3$ is —CN.

In certain embodiments of any of the formulae herein, $R^3$ is hydrogen.

In certain embodiments of any of the formulae herein, L is a divalent $C_{1-6}$ aliphatic which is optionally substituted. In certain embodiments of any of the formulae herein, L is a divalent $C_{3-10}$ aryl which is optionally substituted. In certain embodiments of any of the formulae herein, L is a divalent 3-8 membered saturated or partially unsaturated carbocyclic ring which is optionally substituted. In certain embodiments of any of the formulae herein, L is a divalent 3-7 membered heterocylic ring having 1-4 heteroatoms independently selected from nitrogen, oxygen, or sulfur, which is optionally substituted. In certain embodiments of any of the formulae herein, L is a divalent 5-6 membered monocyclic heteroaryl ring having 1-4 heteroatoms independently selected from nitrogen, oxygen, or sulfur, which is optionally substituted.

In certain embodiments of any of the formulae herein, L is a divalent $C_{1-6}$ aliphatic-$C_{3-10}$ aryl, which is optionally substituted. In certain embodiments of any of the formulae herein, L is a divalent $C_{1-6}$ aliphatic-3-8 membered saturated or partially unsaturated carbocyclic ring, which is optionally substituted. In certain embodiments of any of the formulae herein, L is a divalent $C_{1-6}$ aliphatic-3-7 membered heterocylic ring having 1-4 heteroatoms independently selected from nitrogen, oxygen, or sulfur, which is optionally substituted. In certain embodiments of any of the formulae herein, L is a divalent $C_{1-6}$ aliphatic-5-6 membered monocyclic heteroaryl ring having 1-4 heteroatoms independently selected from nitrogen, oxygen, or sulfur which is optionally substituted.

In certain embodiments, L is a divalent $C_{1-6}$ aliphatic selected from methylene, ethylene, propylene, i-propylene, butylene, s-butylene, t-butylene, straight or branched pentylene, or straight or branched hexylene; each of which is optionally substituted.

In certain embodiments, L is a divalent phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H, 6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, L is

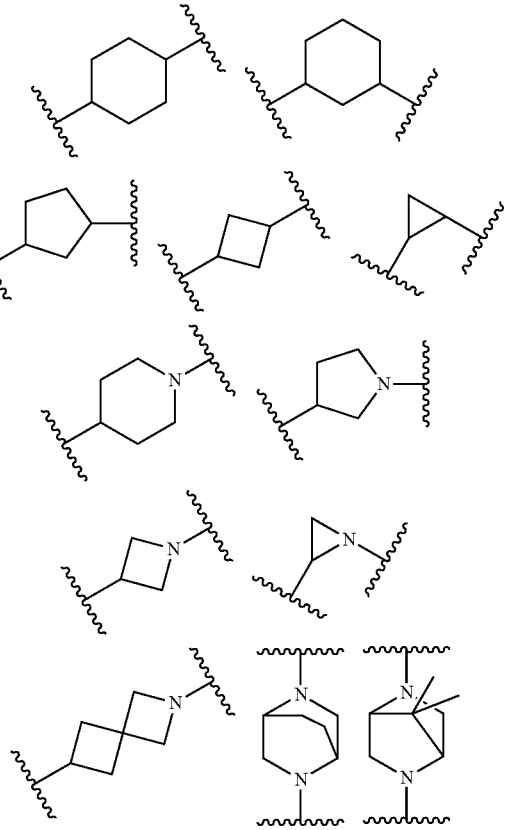

-continued
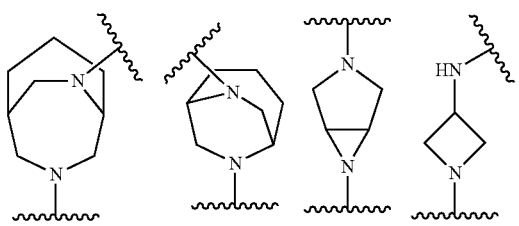
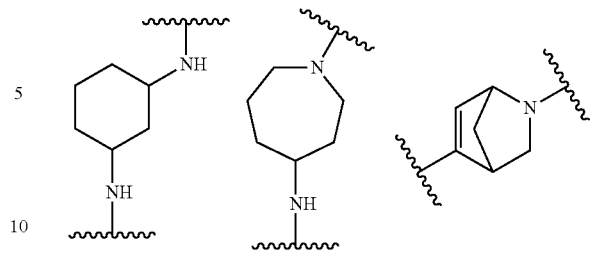

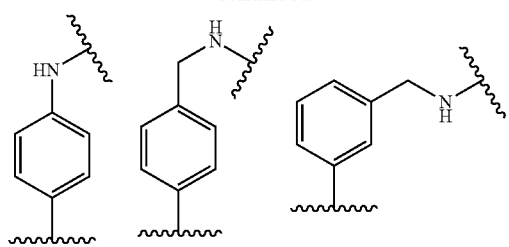
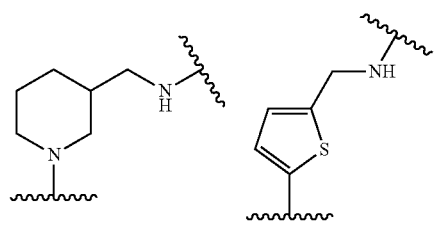
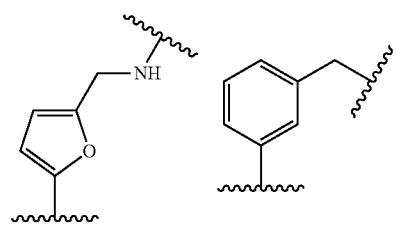
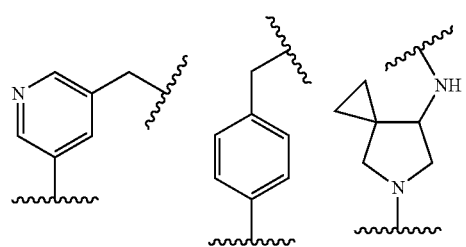
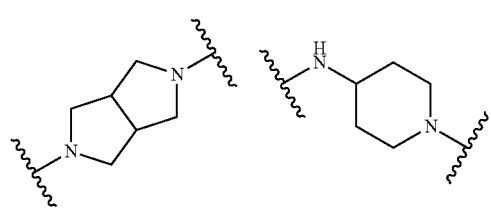
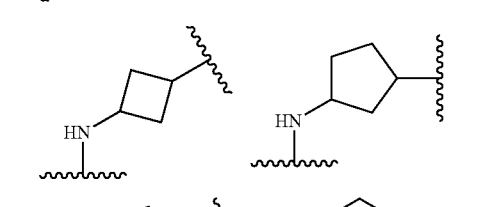
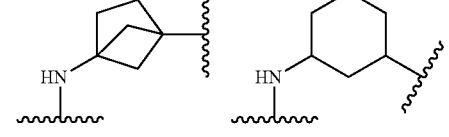
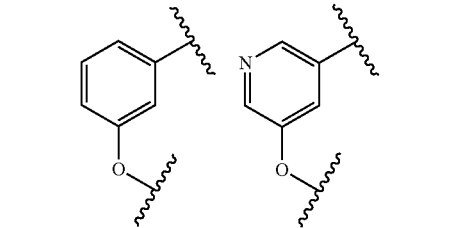
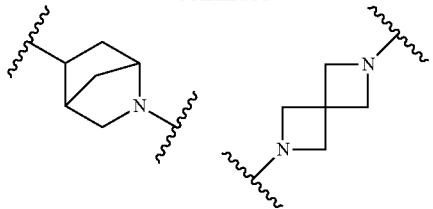
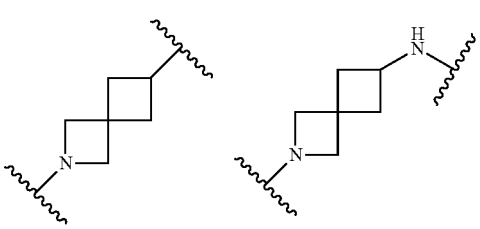
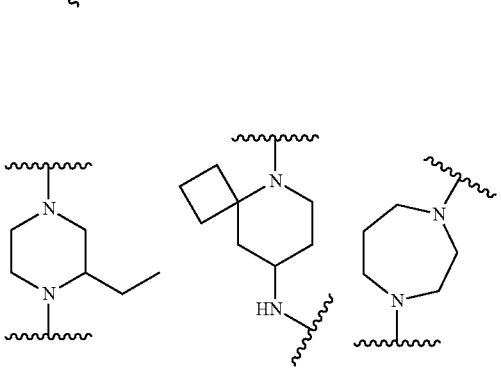
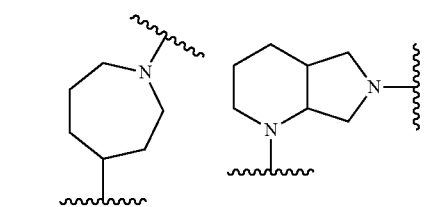
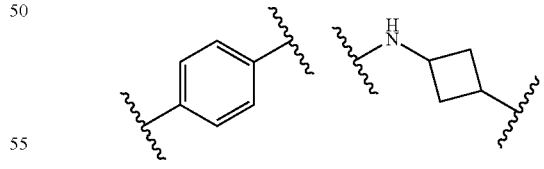
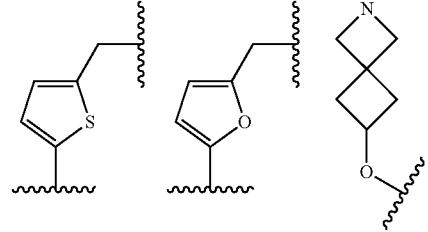

-continued

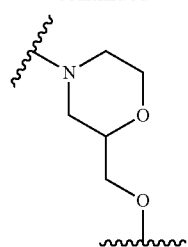

In certain embodiments, L is

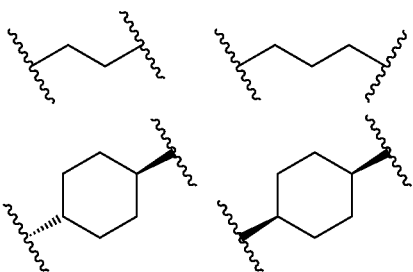

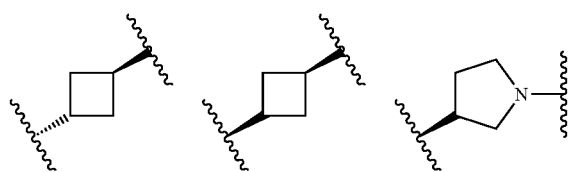

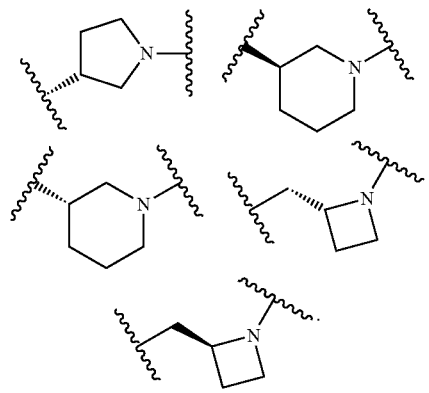

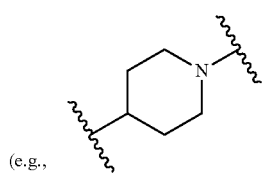 [SMILES: *C1CCN(*)CC1]

For each L described above, the invention contemplates substitution in either direction (e.g., 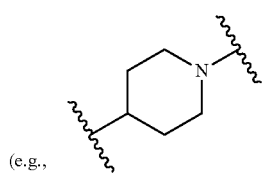 [SMILES: *C1CCN(*)CC1])

indicates either

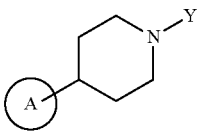

or

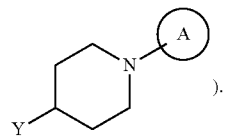

).

In certain embodiments of any of the formulae herein, Y is —NRC(O), —NRC(O)N(R), —NRSO$_2$, or N(R).

In certain embodiments of any of the formulae herein, Y is O, S, SO$_2$, SO, C(O), CO$_2$, or C(O)N(R).

In certain embodiments of any of the formulae herein, Y is absent.

In certain embodiments of any of the formulae herein, Y is

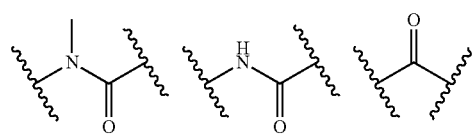

In certain embodiments of any of the formulae herein, $R^1$ is an optionally substituted $C_{1-6}$ aliphatic. In certain embodiments, $R^1$ is an optionally substituted $C_{3-10}$ aryl. In certain embodiments, $R^1$ is an optionally substituted 3-8 membered saturated or partially unsaturated carbocyclic ring. In certain embodiments, $R^1$ is an optionally substituted 3-7 membered heterocylic ring having 1-4 heteroatoms independently selected from nitrogen, oxygen, or sulfur. In certain embodiments, $R^1$ is an optionally substituted 5-6 membered monocyclic heteroaryl ring having 1-4 heteroatoms independently selected from nitrogen, oxygen, or sulfur.

In certain embodiments of any of the formulae herein, $R^1$ is $C_{1-6}$ aliphatic. In certain embodiments, $R^1$ is methyl, ethyl, propyl, i-propyl, butyl, s-butyl, t-butyl, straight or branched pentyl, or straight or branched hexyl; each of which is optionally substituted.

In certain embodiments of any of the formulae herein, $R^1$ is $C_{2-6}$ alkenyl, which is optionally substituted. In certain embodiments, $R^1$ is $C_{2-6}$ alkynyl, which is optionally substituted.

In certain embodiments of any of the formulae herein, $R^1$ is

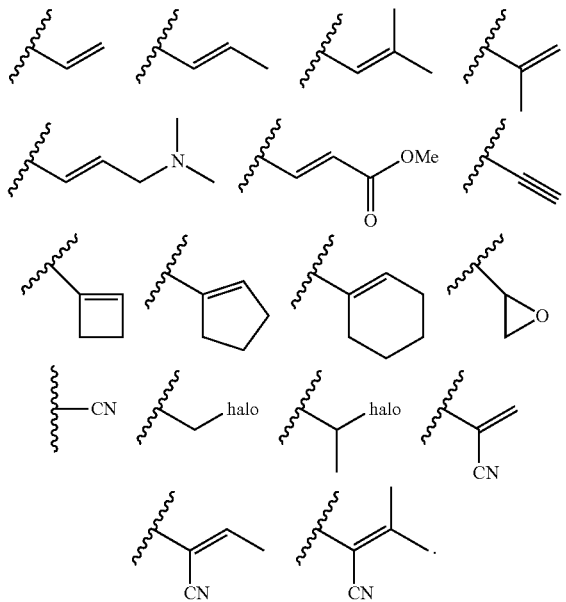

In certain embodiments of any of the formulae herein, X is O, C(O), CO$_2$, C(O)N(R), —NRC(O), —NRC(O)N(R), —NRSO$_2$, or N(R). In certain embodiments, X is O, C(O)N(R), —NRC(O), or N(R). In certain embodiments, X is O, C(O)NH, —NHC(O), NH, or N(Me). In certain embodiments, X is absent.

In certain embodiments of any of the formulae herein, $R^{4'}$ is a divalent $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, $R^{4'}$ is an optionally substituted $C_{1-6}$ aliphatic. In certain embodiments, $R^{4'}$ is an optionally substituted $C_{3-10}$ aryl. In certain embodiments, $R^{4'}$ is an optionally substituted 3-8 membered saturated or partially unsaturated carbocyclic ring. In certain embodiments, $R^{4'}$ is an optionally substituted 3-7 membered heterocyclic ring having 1-4 heteroatoms independently selected from nitrogen, oxygen, or sulfur. In certain embodiments, $R^{4'}$ is an optionally substituted 5-6 membered monocyclic heteroaryl ring having 1-4 heteroatoms independently selected from nitrogen, oxygen, or sulfur.

In certain embodiments, $R^{4'}$ is divalent methyl, ethyl, propyl, i-propyl, butyl, s-butyl, t-butyl, straight or branched pentyl, straight or branched hexyl, or straight or branched heptyl. In certain embodiments, $R^{4'}$ is methyl.

In certain embodiments, $R^{4'}$ is divalent phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^{4'}$ is divalent phenyl, furanyl, furazanyl, imidazolidinyl, imidazolinyl, imidazolyl, 1H-indazolyl, indolenyl, isoxazolyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, or azetidinyl, each of which is optionally substituted.

In certain embodiments, $R^{4'}$ is divalent phenyl, pyridinyl, piperidinyl, or pyrazolyl, each of which is optionally substituted.

In some embodiments, the probe compounds of the present invention comprise a provided compound of any formulae as described herein, tethered to a detectable moiety, $R^t$, by a bivalent tethering moiety, $-T^1-$. The tethering moiety is attached to a compound of the invention via $R^{4'}$.

In some embodiments, $R^t$ is a detectable moiety selected from a primary label or a secondary label. In certain embodiments, $R^t$ is a detectable moiety selected from a fluorescent label (e.g., a fluorescent dye or a fluorophore), a mass-tag, a chemiluminescent group, a chromophore, an electron dense group, or an energy transfer agent. In some embodiments, $R^t$ is biotin, biotin sulfoxide, a radioisotope, or a fluorescent label.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}$P, $^{33}$P, $^{35}$S, $^{14}$C, $^{123}$I, $^{124}$I, $^{125}$I, or $^{131}$I), mass-tags are stable isotopes (e.g., $^{13}$C, $^{2}$H, $^{17}$O, $^{18}$O, $^{15}$N, $^{19}$F, and $^{127}$I), positron emitting isotopes (e.g., $^{11}$C, $^{18}$F, $^{13}$N, $^{124}$I, and $^{15}$O), and fluorescent labels, which are signal generating reporter groups which can be detected without further modifications. Detectable moieties are analyzed by methods. Exemplary methods are fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate includes streptavidin-enzyme or strepavidin-antibody conjugates. For antigen labels, secondary intermediates include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-methoxytetrafluorobenzyl)oxy]phenyl]-3-methylglyceronyl]isonipecotic acid, 4'-[2,3,5,6-tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) are also used as mass-tags. Stable isotopes (e.g., $^{13}$C, $^{2}$H, $^{17}$O, $^{18}$O and $^{15}$N) are also used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion or atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a covalent bond with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety is attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties are directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-$R^r$ moiety. As used herein, "click ready" refers to a moiety containing an azide or alkyne for use in a click chemistry reaction. In some embodiments, the click ready inhibitor moiety comprises an azide. In certain embodiments, the click ready -T-$R^r$ moiety comprises a strained cyclooctyne for use in a copper-free click chemistry reaction (for example, using methods described in Baskin et al., Proc. Natl. Acad. Sci. USA 2007, 104, 16793-16797).

In some embodiments, the detectable moiety, $R^r$, is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, $R^r$ is biotin or an analog thereof. In certain embodiments, $R^r$ is biotin. In certain other embodiments, $R^r$ is biotin sulfoxide.

In another embodiment, $R^r$ is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FLASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -$T^1$-, that attaches the irreversible inhibitor to the detectable moiety. As used herein, the term "tether" or "tethering moiety" refers to any bivalent chemical spacer. Exemplary tethers are a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -$T^1$-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, —NO$_2$, alkyl, S(O), and S(O)$_2$. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -$T^1$-, such as a water soluble polymer is coupled at one end to a provided irreversible inhibitor and to a detectable moiety, R', at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -$T^1$-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form. Exemplary forms are linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range. Exemplary ranges are between about 100 Da and about 100,000 Da or more. In yet further embodiments, the molecular weight of the polymer is between about 100 Da and about 100,000 Da, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da. Exemplary ranges are about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

In certain embodiments, the tethering moiety, -T¹-, has the following structure:

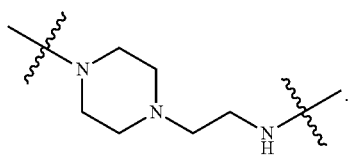 [SMILES: *NCCN1CCN(*)CC1]

In certain embodiments, the tethering moiety, -T¹-, has the following structure:

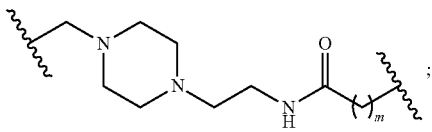

wherein m is 0, 1, 2, 3, 4, 5, 6, or 7.

In certain embodiments, —R$^t$ is quinine, phenylalanine, tyrosine, trptophan, NADH, FMN, EDANS, Lucifer Yellow, pyrene, 4-MU, AMC, DAPI, Hoechst33342, NBD, bimane, Cascade yellow, fluorescein, RH110, TMR, SRh101, naphthofluorescein, SNARF-1, propidium, BODIPY-FL, BODIPY-TR, Cy3, Cy5, Cy7, IRDye 700DX, or resorufin.

In some embodiments, -T¹-R$^t$ is of the following structure:

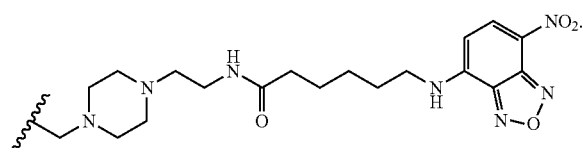 [SMILES: *CN1CCN(CCNC(=O)CCCCCNc2ccc([N+](=O)[O-])c3nonc23)CC1]

In some embodiments, -T¹-R$^t$ is of the following structure:

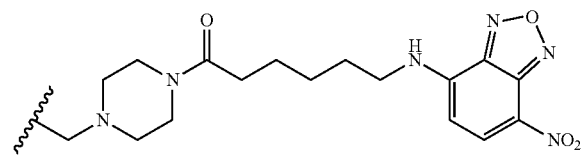 [SMILES: *CN1CCN(C(=O)CCCCCNc2ccc([N+](=O)[O-])c3nonc23)CC1]

In certain embodiments, -T¹-R$^t$ is of the following structure:

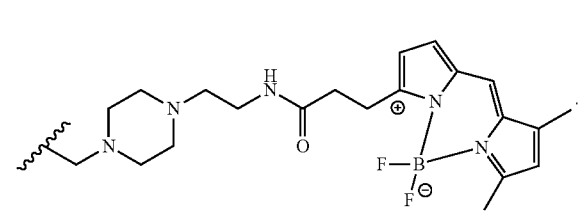

In certain embodiments, -T¹-R$^t$ is of the following structure:

In certain embodiments, -T¹-R$^t$ is of the following structure:

In certain embodiments, -T¹-R$^t$ is of the following structure:

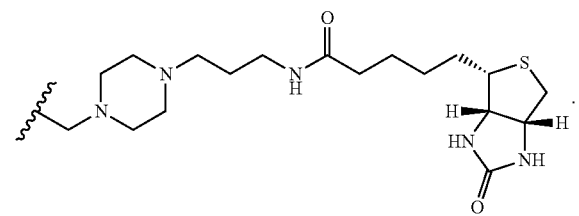 [SMILES: *CN1CCN(CCCNC(=O)CCCC[C@@H]2SC[C@@H]3NC(=O)N[C@@H]32)CC1]

In certain embodiments, -T¹-R$^t$ is of the following structure:

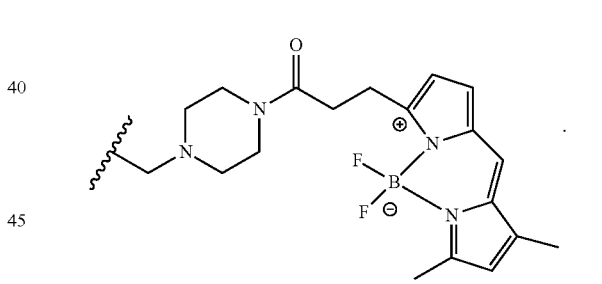

In certain embodiments, -T¹-R$^t$ is of the following structure:

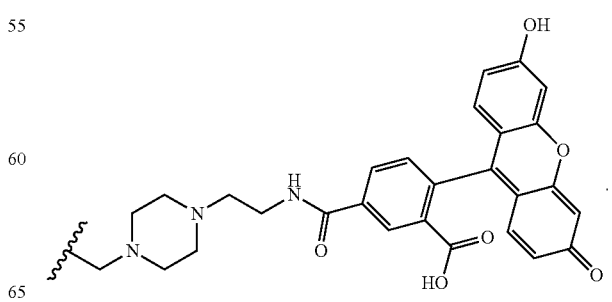

In certain embodiments, -T¹-R' is of the following structure:

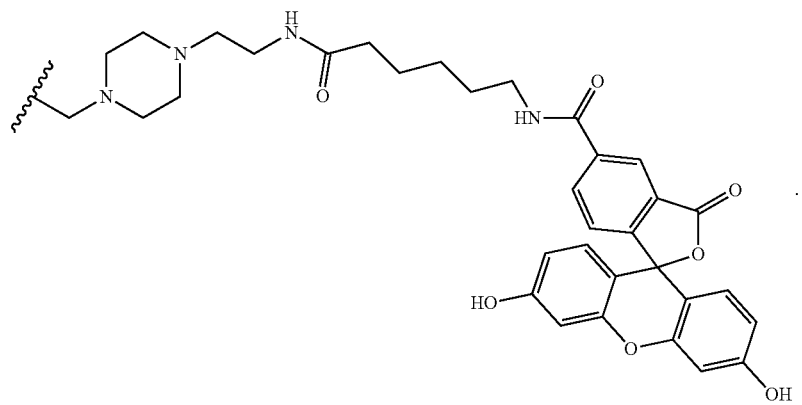 [SMILES: *CN1CCN(CCNC(=O)CCCCCNC(=O)c2ccc3c(c2)C(=O)OC32c3ccc(O)cc3Oc3cc(O)ccc32)CC1]

In certain embodiments, -T¹-R' is of the following structure:

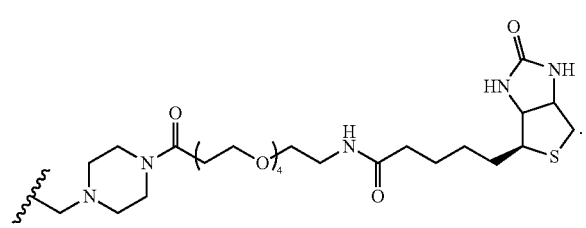

In certain embodiments, -T¹-R' is of the following structure:

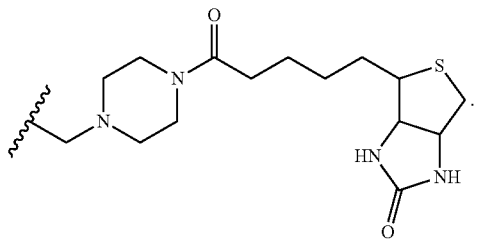 [SMILES: *CN1CCN(C(=O)CCCCC2SCC3NC(=O)NC32)CC1]

It will be appreciated that many -T¹-R' reagents are commercially available.

In some embodiments, the present invention provides a method for determining occupancy of a protein kinase by a provided irreversible inhibitor in a patient, comprising providing one or more tissues, cell types, or a lysate thereof, obtained from a patient prior to any dose of a compound of said irreversible inhibitor; providing one or more tissues, cell types, or a lysate thereof, obtained from a patient administered at least one dose of a compound of said irreversible inhibitor, contacting said tissue, cell type or lysate thereof with a probe compound (i.e., a compound of formula I) to covalently modify at least one protein kinase present in said lysate, and measuring the amount of said protein kinase covalently modified by the probe compound to determine occupancy of said protein kinase by said inhibitor as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

In some embodiments, the present invention provides a method for determining occupancy of a protein kinase by a provided irreversible inhibitor in a patient, comprising providing one or more tissues, cell types, or a lysate thereof, obtained from a patient administered at least one dose of a compound of said irreversible inhibitor, contacting said tissue, cell type or lysate thereof with a probe compound (i.e., a compound of formula I) to covalently modify at least one protein kinase present in said lysate, and measuring the amount of said protein kinase covalently modified by the probe compound to determine occupancy of said protein kinase by said inhibitor as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is BTK.

In some embodiments, the probe compound comprises the irreversible inhibitor for which occupancy is being determined.

In certain embodiments, the BTK inhibitors compound is an irreversible inhibitor. In certain embodiments, the BTK inhibitor compound comprises a Michael acceptor moiety.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In some embodiments, the probe is detected by sodium dodecyl sulfate polyacrylamide gel electrophoresis (SDS-PAGE). In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of any of the formulae presented herein, wherein the assaying step comprises contacting said one or more tissues, cell types, or a lysate thereof, with a provided probe compound and measuring the amount of protein kinase covalently modified by the probe compound.

In some embodiments, the invention provides a method of determining an efficacious dose for treating a BTK-mediated disease or disorder in a subject, the method comprising administering to the subject an amount of a BTK inhibitor, collecting a biological sample from the subject, contacting the sample with a probe to form a probe-bound BTK kinase, detecting the amount of probe-bound BTK kinase in the sample, determining target occupancy of the BTK kinase based on the amount of probe-bound kinase detected in the sample, and determining the dose of the BTK inhibitor that causes an increase in efficacy.

In some embodiments, the invention provides a method as described above, further comprising repeating the steps with different amounts of BTK inhibitor, to determine a dosing profile.

In certain embodiments, the measurement after administration of the BTK inhibitor is made 1 hour to 8 weeks after said administration. In certain embodiments, the measurement after administration of the BTK inhibitor is made 1 hour to 4 weeks after said administration. In certain embodiments, the measurement after administration of the BTK inhibitor is made 0 to 10 hours after said administration. In certain embodiments, the measurement after administration of the BTK inhibitor is made 5 minutes to 8 hours after said administration.

In certain embodiments, the level of BTK occupancy is detected in vitro using a compound of any of the formulae herein.

In certain embodiments, the level of BTK is measured using blood or a biological tissue sample from the patient/subject.

In certain embodiments, the level of BTK occupancy is measured using immunofluorescence. In certain embodiments, level of BTK occupancy is measured using immunoblotting methodology. In certain embodiments, level of BTK occupancy is measured using an ELISA assay. In certain embodiments, level of BTK occupancy is measured using SDS-PAGE.

In certain embodiments, the invention provides a method for selecting a patient for treatment for a BTK-related disease/disorder, with a BTK inhibitor, comprising measuring BTK levels or BTK transcriptional target levels in a patient sample using a BTK occupancy assay, correlating a high level of BTK or BTK transcriptional target levels with a positive response to the treatment, and selecting or excluding the patient for treatment based on the BTK level or BTK transcriptional target levels.

In certain embodiments, the invention provides a method for measuring a patient's response to treatment comprising administering to the patient a BTK inhibitor, measuring BTK levels or BTK transcriptional target levels in a patient sample using a BTK occupancy assay, correlating a reduced level of BTK or BTK transcriptional targets with a positive response to the administration of the BTK inhibitor, and continuing or stopping treatment of the patient with the compound based on the BTK levels or the BTK transcriptional target levels.

In certain embodiments, the invention provides a method for determining a dosing schedule in a subject, comprising the steps of i) increasing the dosage of the BTK kinase inhibitor if the target occupancy is less than about 50%, ii) decreasing the dosage of the BTK kinase inhibitor if the target occupancy is above at least about 70%, iii) maintaining the same therapeutic regimen of the BTK kinase inhibitor or iv) discontinuing the therapeutic regimen.

In certain embodiments, the invention provides a method for determining the efficacy of the BTK kinase inhibitor therapy based on the target occupancy, wherein the BTK kinase inhibitor is i) effective when the occupancy of the BTK kinase is at least about 70% or ii) ineffective when the occupancy of the BTK kinase is less than about 50%.

In certain embodiments, the invention provides a method as described above, further comprising capturing probe-bound kinase with a capture agent. In certain embodiments, the capture target is streptavidin or an antibody. In various embodiments, the capture target is attached to a solid support. In various embodiments, the solid support is a plate, a microplate, a bead or a plurality of beads.

In certain embodiments, the invention provides a method as described above, further comprising contacting the probe-bound kinase with a primary detection agent, and optionally, a secondary detection agent that binds to the primary detection agent. In certain embodiments, the primary detection agent or secondary detection agent comprises an antibody, a bead, a dye, a label, a tag, a fluorophore, or any combination thereof. In certain embodiments, the primary detection agent is an anti-BTK antibody, an anti-ITK antibody, an anti-TXK antibody, anti-TEC antibody, anti-BMX antibody, or anti-BLK antibody. In a further embodiment, the primary or secondary detection agent is conjugated to a chemiluminescent tag.

In certain embodiments, each of $R^1$, $R^2$, $R^3$, $R^{4'}$, $T^1$, $R^t$, X, Y, and L is as defined above and described in embodiments, classes and subclasses above and herein, singly or in combination.

In certain embodiments, the probe is a compound of formula I-a1,

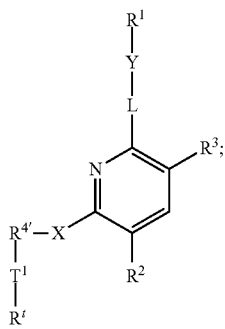

I-a1 or a pharmaceutically acceptable salt thereof, wherein each of $R^1$, $R^2$, $R^3$, $R^{4'}$, $T^1$, $R^t$, X, L and Y is as defined above and described in embodiments, classes and subclasses above and herein, singly or in combination.

In certain embodiments, the present invention provides a compound of formula I-a2,

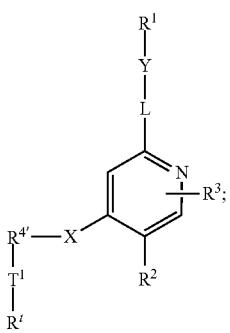

I-a2 or a pharmaceutically acceptable salt thereof, wherein each of $R^1$, $R^2$, $R^3$, $R^{4'}$, $T^1$, $R^t$, X, L and Y is as defined above and described in embodiments, classes and subclasses above and herein, singly or in combination.

In certain embodiments, the present invention provides a compound of formula I-a3,

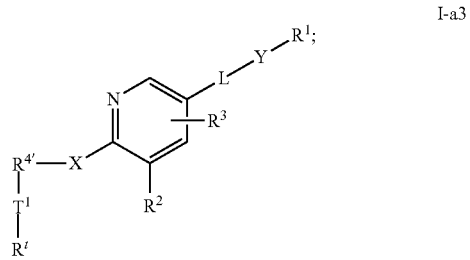

I-a3 or a pharmaceutically acceptable salt thereof, wherein each of $R^1$, $R^2$, $R^3$, $R^{4'}$, $T^1$, $R^t$, X, L and Y is as defined above and described in embodiments, classes and subclasses above and herein, singly or in combination.

In certain embodiments, the present invention provides a compound of formula I-a4,

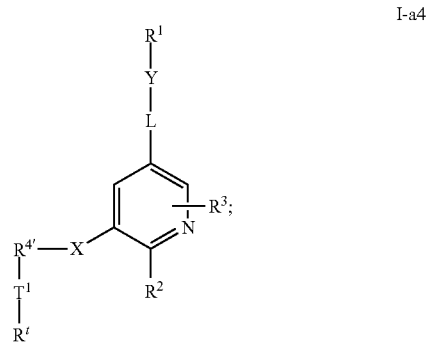

I-a4 or a pharmaceutically acceptable salt thereof, wherein each of $R^1$, $R^2$, $R^3$, $R^{4'}$, $T^1$, $R^t$, X, L and Y is as defined above and described in embodiments, classes and subclasses above and herein, singly or in combination.

In certain embodiments, the present invention provides a compound of formula I-a5,

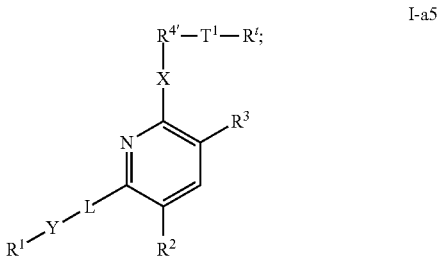

I-a5 or a pharmaceutically acceptable salt thereof, wherein each of $R^1$, $R^2$, $R^3$, $R^{4'}$, $T^1$, $R^t$, X, L and Y is as defined above and described in embodiments, classes and subclasses above and herein, singly or in combination.

In certain embodiments, the assay comprises a probe compound (the probe compound is a BODIPY-labeled probe or a Biotin-labeled probe), and assay methods that use the different probes for measuring Btk occupancy. In certain embodiments, the binding of the BODIPY-tagged probe to the active site of Btk is measured using a SDS-PAGE based method. In certain embodiments, the binding of the biotinylated probe to Btk is detected using a modified ELISA that employs 96 well plates coated with streptavidin. In certain embodiments, the biotin-streptavidin assay is performed as a traditional ELISA format where detection is accomplished using an HRP-tagged secondary antibody. In other embodiments, the assay is run on the Meso Scale Discovery (MSD) platform and an antibody labeled with a SULFO-tag is used for detection.

In certain embodiments, the invention provides a compound selected from Table 1:

TABLE 1

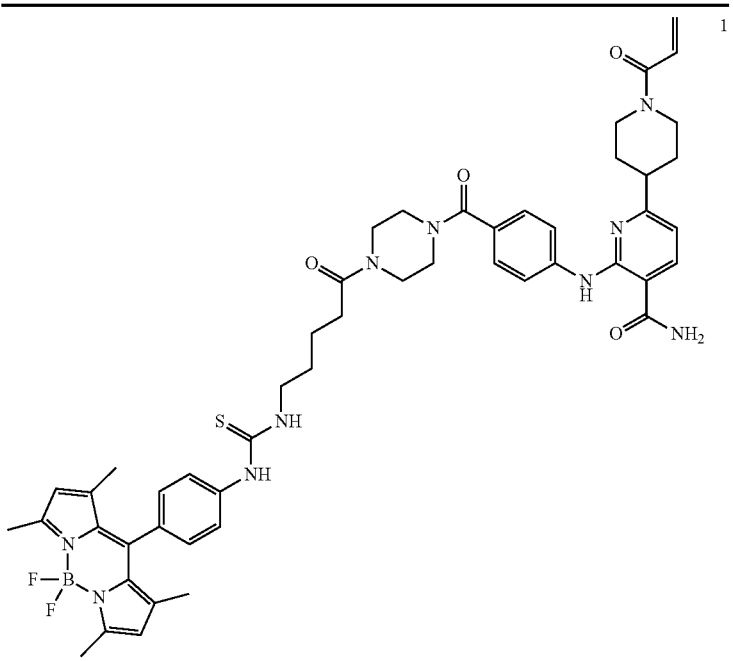

1

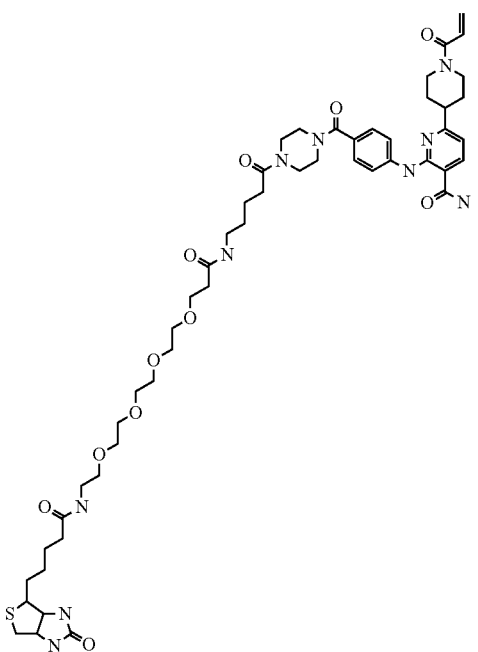 [SMILES: C=CC(=O)N1CCC(c2ccc(C(N)=O)c(Nc3ccc(C(=O)N4CCN(C(=O)CCCCNC(=O)CCOCCOCCOCCOCCNC(=O)CCCCC5SCC6NC(=O)NC65)CC4)cc3)n2)CC1]

2

As defined generally above, the group "L-Y—R$^1$" is a warhead group. Without wishing to be bound by any particular theory, it is believed that such warhead groups are particularly suitable for covalently binding to a key cysteine residue in the binding domain of certain protein kinases. Protein kinases having a cysteine residue in the binding domain are known to one of ordinary skill in the art and include BTK, or a mutant thereof. Thus, in some embodiments, L-R$^1$ is characterized in that the L-R$^1$ moiety is capable of covalently binding to a cysteine residue thereby irreversibly inhibiting the enzyme. In certain embodiments, the cysteine residue in the kinase domain is in the ATP biding site. In certain embodiments, the cysteine residue is Cysteine-481.

Various structural depictions may show a heteroatom without an attached group, radical, charge, or counterion. Those of ordinary skill in the art are aware that such depictions are meant to indicate that the heteroatom is attached to hydrogen (e.g. 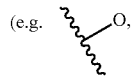

is understood to be

 )

In certain embodiments, the compounds of the invention were synthesized in accordance with the schemes provided in the Examples below.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade). All reactions were conducted at room temperature unless otherwise noted. All compounds of the present invention were synthesized by processes developed by the inventors.

$^1$H-NMR spectra were recorded on a Bruker Avance III 400 MHz. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), m (multiplet), or br (broad).

Mass spectra were obtained on Agilent 1200 Series mass spectrometers from Agilent technologies, using either Atmospheric Chemical Ionization (APCI) or Electrospray Ionization (ESI). Column: XBridge C8, 3.5 μm, 4.6×50 mm; Solvent A: water+0.1% TFA; Solvent B: CAN; Flow: 2 ml/min; Gradient: 0 min: 5% B, 8 min: 100% B, 8.1 min: 100% B, 8.5 min: 5% B, 10 min 5% B.

HPLC data were obtained using Agilent 1100 series HPLC from Agilent technologies using XBridge column (C8, 3.5 μm, 4.6×50 mm). Solvent A: water+0.1% TFA; Solvent B: ACN; Flow: 2 ml/min; Gradient: 0 min: 5% B, 8 min: 100% B, 8.1 min: 100% B, 8.5 min: 5% B, 10 min 5% B.

The microwave reactions were conducted using Biotage Initiator Microwave Synthesizer using standard protocols that are known in the art.

Example 1

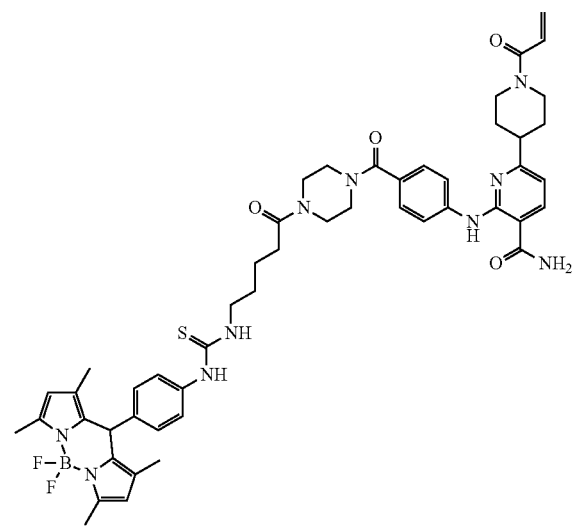

1'-Acryloyl-6-{4-[4-(5-{3-[4-(4,4-difluoro-1,3,5,7-tetramethyl-3a,4alambda4-diaza-4lambda4-bora-s-indacen-8-yl)-phenyl]-thioureido}-pentanoyl)-piperazine-1-carbonyl]-phenylamino}-1',2',3',4',5',6'-hexahydro-[2,4']bipyridinyl-5-carboxylic acid amide (1)

1'-Acryloyl-6-{4-[4-(5-amino-pentanoyl)-piperazine-1-carbonyl]-phenylamino}-1',2',3',4',5',6'-hexahydro-[2,4']bipyridinyl-5-carboxylic acid amide hydrochloride (0.14 mmol; 1.00 eq.; 83.00 mg) was combined with 4,4-Difluoro-8-(4-isothiocyanato-phenyl)-1,3,5,7-tetramethyl-3a, 4alambda4-diaza-4lambda4-bora-s-indacene (0.15 mmol; 1.10 eq.; 58.19 mg) and Hünig's base (0.42 mmol; 3.00 eq.; 53.77 mg; 0.07 ml) into a mixture of MeCN (38.29 mmol; 275.95 eq.; 1572.00 mg; 2.00 ml) and MeOH (12.34 mmol; 88.95 eq.; 395.50 mg; 0.50 ml). The mixture was stirred at RT for 1.5 hrs. All solvent was then removed and the material was purified on silica (15 micron) using a gradient of 0-20% MeOH in DCM to give 1'-Acryloyl-6-{4-[4-(5-{3-[4-(4,4-difluoro-1,3,5,7-tetramethyl-3a,4alambda4-diaza-4lambda4-bora-s-indacen-8-yl)-phenyl]-thioureido}-pentanoyl)-piperazine-1-carbonyl]-phenylamino}-1',2',3',4',5',6'-hexahydro-[2,4']bipyridinyl-5-carboxylic acid amide (56.00 mg, 42%). HPLC: 99%, RT=6.46 min. MS: m/z=943 [M+H]+. $^1$H NMR (400 MHz, Chloroform-d) δ 10.91 (s, 1H), 7.98 (bs, 1H), 7.87-7.77 (m, 2H), 7.73 (d, J=7.9 Hz, 1H), 7.51-7.36 (m, 4H), 7.36-7.25 (m, 4H), 6.85 (s, 1H), 6.73-6.58 (m, 2H), 6.31 (dd, J=16.8, 2.0 Hz, 1H), 5.99 (s, 2H), 5.73 (dd, J=10.6, 2.0 Hz, 1H) 4.81-4.65 (m, 2H), 4.23-4.08 (m, 2H), 3.83-3.47 (m, 12H), 3.31-3.15 (m, 1H), 3.00-2.72 (m, 2H), 2.56 (s, 3H), 2.50-2.37 (m, 2H) 2.11-1.97 (m, 2H), 1.89-1.67 (m, 4H), 1.42 (s, 3H), 1.61 (s, 6H).

Example 2

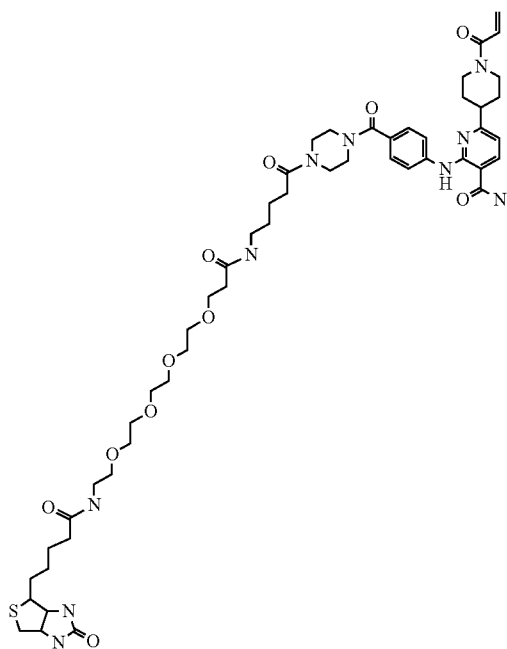 [SMILES: C=CC(=O)N1CCC(c2ccc(C(N)=O)c(Nc3ccc(C(=O)N4CCN(C(=O)CCCCNC(=O)CCOCCOCCOCCOCCNC(=O)CCCCC5SCC6NC(=O)NC65)CC4)cc3)n2)CC1]

6-(1-acryloylpiperidin-4-yl)-2-((4-(4-(5,21-dioxo-1-(2-oxohexahydro-1H-thieno[3,4-d]imidazol-4-yl)-9,12,15,18-tetraoxa-6,22-diazaheptacosan-27-oyl)piperazine-1-carbonyl)phenyl)amino)nicotinamide (2)

1'-Acryloyl-6-{4-[4-(5-amino-pentanoyl)-piperazine-1-carbonyl]-phenylamino}-1',2',3',4',5',6'-hexahydro-[2,4']bipyridinyl-5-carboxylic acid amide hydrochloride (0.13 mmol; 1.00 eq.; 80.00 mg), described above, was combined with 3-{2-[2-(2-{2-[5-(2-Oxo-hexahydro-thieno[3,4-d]imidazol-4-yl)-pentanoylamino]-ethoxy}-ethoxy)-ethoxy]-ethoxy}-propionic acid 2,5-dioxo-pyrrolidin-1-yl ester (0.14 mmol; 1.01 eq.; 79.52 mg; 0.07 ml) and Hünig base (0.40 mmol; 3.00 eq.; 51.82 mg; 0.07 ml) into MeCN. The mixture was then heated to 60° C. for 1 hr. The reaction was then purified via column chromatography using a gradient of 0-15% MeOH/DCM to give 6-(1-acryloylpiperidin-4-yl)-2-((4-(4-(5,21-dioxo-1-(2-oxohexahydro-1H-thieno[3,4-d]imidazol-4-yl)-9,12,15,18-tetraoxa-6,22-diazaheptacosan-27-oyl)piperazine-1-carbonyl)phenyl)amino)nicotinamide (44.00 mg, 32%). HPLC: 99%, RT=6.46 min. MS: m/z=1035 [M+H]+. $^1$H NMR (400 MHz, MeOD) δ 8.06 (d, J=7.9 Hz, 1H), 7.88 (d, J=8.7 Hz, 2H), 7.44 (d, J=8.7 Hz, 2H), 6.94-6.71 (m, 2H), 6.24 (dd, J=16.8, 2.0 Hz, 2H), 5.78 (dd, J=10.6, 2.0 Hz, 1H), 5.48 (dt, J=34.5, 22.2 Hz, 2H), 4.50 (dd, J=12.9, 5.2 Hz, 1H), 4.43-4.25 (m, 2H), 3.80-3.51 (m, 15H), 3.39-3.34 (m, 4H), 3.22 (dd, J=23.8, 17.0 Hz, 3H), 3.06-2.84 (m, 3H), 2.47 (dt, J=12.3, 5.7 Hz, 3H), 2.37-2.01 (m, 4H), 1.86-1.53 (m, 7H), 1.54-1.27 (m, 4H).

Example 3

Human Blood Used in a Btk Occupancy Experiment with the Biotinylated Probe and the MSD Platform. Blood was collected from a single human donor into a CPT™ tube and PBMCs were isolated and frozen. After thawing, cells were divided into 3 tubes. One tube received no treatment (No Probe), one tube was treated with 1 µM 2 (+Probe), and one tube was treated for 10 min with 1 µM of a representative irreversible Btk inhibitor, followed by 1 µM 2 (+Probe+BTK inhibitor). Incubations with probe were performed for 1 hr at 37 C. Cells were then lysed and analyzed for BTK-biotin by MSD assay. The results are found in FIG. 1.

We claim:
1. A method for determining drug target occupancy of a BTK inhibitor compound, comprising:
   (a) contacting a sample comprising a mixture of BTK kinase and a BTK inhibitor compound, with a probe to form a probe-bound kinase;
   (b) detecting the amount of probe-bound kinase in the sample; and
   (c) determining the occupancy of the BTK inhibitor compound based on the amount of probe-bound kinase detected in the sample;
wherein the probe is:

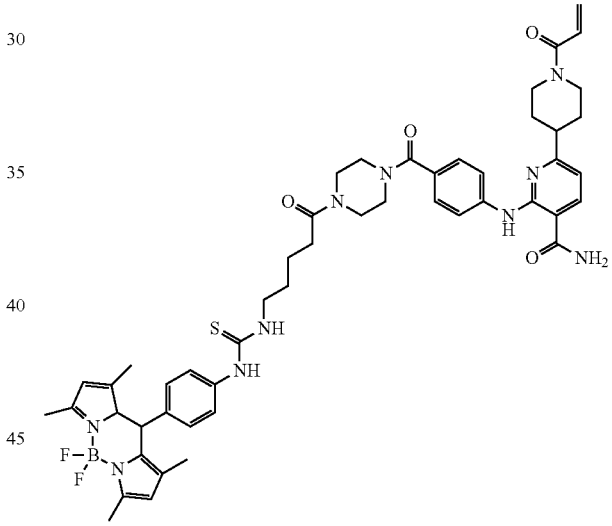

or

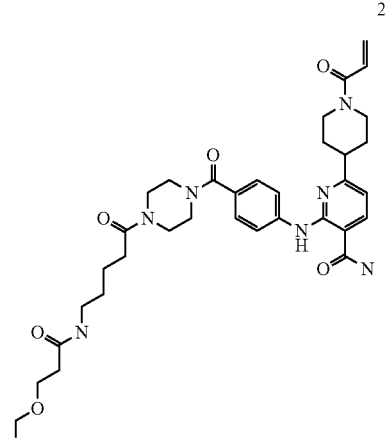

-continued

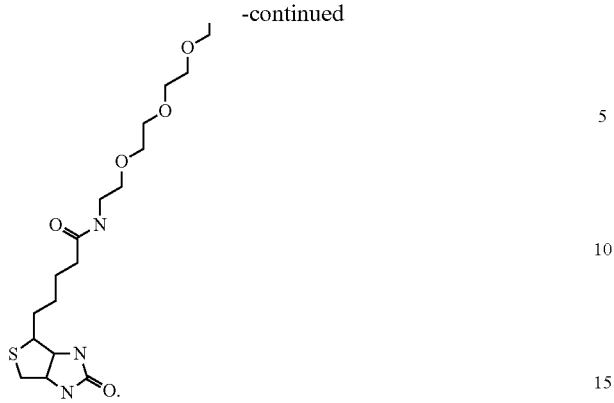

2. The method of claim 1, wherein the step of determining target occupancy comprises determining the number of binding sites not occupied by the BTK kinase inhibitor based on the amount of probe-bound kinase detected in the sample.

3. The method of claim 1, further comprising a step of determining or modifying a therapeutic regimen based on the target occupancy of the BTK kinase.

4. The method of claim 1, further comprising a step of performing the method at two or more time points.

* * * * *